United States Patent [19]

Levenson

[11] Patent Number: 5,276,180
[45] Date of Patent: Jan. 4, 1994

[54] PROCESS FOR MAKING SUCCINYL ACETONE

[75] Inventor: Corey H. Levenson, Oakland, Calif.

[73] Assignee: Cetus Oncology Corporation, Emeryville, Calif.

[21] Appl. No.: 403,338

[22] Filed: Sep. 6, 1989

[51] Int. Cl.$^5$ ............................................ C07C 59/147
[52] U.S. Cl. .................................................... 562/577
[58] Field of Search ........................................ 562/577

[56] References Cited

PUBLICATIONS

Pendarvis et al, J. Org. Chem. 39: 2289–2291 (1974).
Battersby et al., J. C. S. Perkin I, 1981: 2786–2792.
Treibs et al, Chem. Berichte, 87:1163–1166 (1954).
Reeve, et al., 1979, Can. J. Chem., 57:2747–2754.
Olmstead, et al., 1980, J. Org. Chem., 45:3295–3299.
Buncel and Menon, 1977, J. of Amer. Chem. Soc., 99:4457–4461.
Buncel and Menon, 1977, J. Org. Chem., 141:1–7.
Harned and Robinson, 1940, Trans. Faraday Soc., 36:973–978.
Hauser et al., 1954, *Organic Reactions* 8:108–109.
Treibs and Hintermeiser, Jun. 9, 1954, *Syntheses with Acetoacetic Acid Tert-Butyl Ester* (lecture delivered at the Chemical Teachers' Convention in Aachen, May 1, 1953).

*Primary Examiner*—José G. Dees
*Assistant Examiner*—Joseph M. Conrad, III
*Attorney, Agent, or Firm*—Philip L. McGarrigle

[57] ABSTRACT

The present invention is a simplified process for making succinyl acetone (SA). The most preferred embodiment is a one step process that reacts levulinic acid, ethyl acetate, and a base to form SA. Generally, a levulinic acid group may be reacted with an alkyl ester and a base to form SA. Optionally, the reaction may be acidified after completion to remove byproducts.

11 Claims, No Drawings

PROCESS FOR MAKING SUCCINYL ACETONE

TECHNICAL FIELD OF THE INVENTION

This invention relates to a process for making a chemical compound that is useful in the area of immunology. Specifically, the process is used to make an immunosuppressive drug that is useful to treat a wide variety of diseases arising from a normal or dysfunctional immune response.

BACKGROUND OF THE INVENTION

There is a continuous search for therapeutics that have immunosuppressive activity, and therefore facilitate organ tissue transplants, as well as being beneficially applied to the treatment of autoimmune or graft versus host disease. The basis of organ tissue rejection is known and resides in the histocompatibility two locus (H-2) in the mouse, and the human leucocyte antigen (HLA) complex in the human. Klein, J., et al. *Ann. Rev. Immunol.* 1:119 (1983). Both systems code for cell surface molecules that are recognized as foreign in a recipient host. Only in those instances where the donor and recipient are genetically identical, that is when the donor and recipient are identical twins, is there little or no chance of rejection of the transplanted organ. However, since the donor and recipient are rarely genetically identical, some degree of histocompatibility antigenic mismatch is present, and hence the application of immunosuppressive drugs is required. This is true, even where donors and recipients are HLA matched, that is, matched with the antigens of the major histocompatibility complex loci, since rejection of the transplant can still arise as a result of mismatching of minor genetic loci that are also involved in rejection.

Immunosuppressive drugs are also widely used in the area of graft versus host rejection, particularly bone marrow transplants. The graft from a donor contains a significant number of immunocompetent lymphoid cells that can mount an effective destructive reaction against host cells. Bone marrow transplants are often employed to treat various malignant diseases, including leukemia. Generally this involves immunologically crippling the leukemic patient, and then transplanting bone marrow from a donor. Unless the lymphoid cells in the donor marrow are suppressed they can react against recipient tissue antigens, often with dire consequences. A variety of drugs, and antisera to lymphoid cells are used as immunosuppressives. Particularly useful drugs are corticosteroids, othiopirne, and cyclosporine. Various monoclonal antibodies, alone or when coupled to a cytotoxic agent, are available for eliminating lymphoid cells from the donor marrow. P. S. Russell et al., *Annual Review Medicine* 35:63 (1984). Not only are these immunosuppressive drugs used in the area of organ tissue transplantation and graft versus host disease, they are also widely sought after to treat autoimmune diseases.

Another drug that is useful in the above context is succinyl acetone (4, 6-dioxoheptanoic acid, hereinafter referred to as SA). For example, U.S. Pat. No. 4,670,467 claims SA as an immunosuppressive medicament and *Clin. Imm. and Immunopath.*, 49:63-71 (1988) describes SA in the treatment of experimental autoimmune disease. Also, Hess et al., *Jour. of Immunol.* 139:2845-2849 (1987), discloses that graft versus host disease may be treated with SA. Against this background, it is evident that SA is a compound that is useful to treat disease. As a consequence, processes for making SA are also important.

In the prior art, SA has been made in a variety of ways. See U.S. patent application Ser. No. 324,360 which is hereby incorporated by reference in its entirety and Pendarvis et al., J. Org. Chem., 39:2289-2291 (1974). Also, SA can be prepared from simple esters, i.e. methyl (Battersby, et al., *J. C. S. Perkin I*, 1981:2786-2792) and ethyl (Treibs et al., *Chem. Berichte*, 87:1163-1166 (1954)). Generally, they can be complicated procedures that involve multiple steps, different reagents, and reaction conditions. Obviously, if a process is complex, then it can be expensive and provide more opportunities for mistakes. Consequently, there is always a need to simplify the process that is used to make a chemical compound such as SA. That need is satisfied by the invention that is described below.

SUMMARY OF THE INVENTION

The present invention is a process for making Succinyl Acetone (SA) comprising reacting levulinic acid and ethyl acetate, at the appropriate reaction conditions, in the presence of a base to make SA. The invention further comprises acidifying the SA containing reaction mixture. Preferably, the base is selected from the group consisting essentially of lithium or sodium amide, sodium or potassium hydride, or sodium or potassium alkoxides, such as methoxide, ethoxide, and t-butoxide. Preferably, the acid is selected from the group consisting essentially of hydrochloric, sulfuric, phosphoric, and acetic acids.

Among other factors, the present process is advantageous because it is less labor intensive (there is no distillation, chromatography, etc.), very inexpensive, and less open to error.

More specifically, the present invention is a process for making Succinyl Acetone (SA) comprising reacting one part levulinic acid to at least three parts base in the presence of ethyl acetate, at the appropriate reaction conditions, to make SA, and acidifying the solution containing SA.

DESCRIPTION OF THE INVENTION

As stated above, the present invention is a process for making SA. SA is a seven carbon, organic keto-acid that has the following formula:

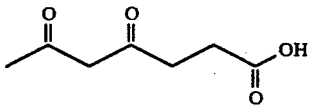

The starting materials for the present SA synthesis are levulinic acid and an acetylating reagent, such as an acetic acid ester (or compounds containing those groups). Preferable acetic acid esters are alkyl esters, such as methyl, ethyl, propyl acetate, etc. As discussed in The Merck Index (monograph no. 5304), levulinic acid is also called 4-oxopentanoic acid and is produced from low grade cellulose. Levulinic acid is also commercially available from chemical suppliers, such as Aldrich. It has the following formula:

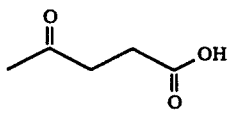

As discussed in The Merck Index (monograph no. 3606) ethyl acetate is also called acetic acid ethyl ester or acetic ether. It can be produced by the slow distillation of acetic acid, ethyl alcohol, and sulfuric acid (see U.S. Pat. No. 2,787,636). It has the following formula:

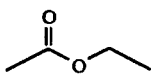

Levulinic acid and ethyl acetate are reacted in the presence of a base. The base must be able to catalyze the reaction between the two reactants to form SA. It is preferable that the base does not compete with levulinic acid as a reagent, i.e. it does not act as a nucleophile. Preferably, the base is: lithium or sodium amide; sodium or potassium hydride; or sodium or potassium alkoxides, such as methoxide, ethoxide, and t-butoxide. Preferably, the acid is selected from the group consisting essentially of hydrogen chloride, sulfuric, phosphoric, and acetic acids.

The above reagents may be added in a wide range of concentrations to produce SA. However, it is preferred that the reaction mixture contain one part levulinic acid to a minimum of three parts base. Preferably the ethyl acetate is added to excess as it is inexpensive and acts as a solvent. It is also preferable to stir and cool the reaction mixture.

After the reaction has occurred and SA has formed, an acid is preferably added to acidify the ethoxide to a salt (i.e. sodium hydroxide, if hydrochloric acid and sodium hydride are used) and ethanol. Thereafter, the SA can be recovered in the organic phase, while the sodium chloride and most of the ethanol can be recovered in the aqueous phase.

The following reaction scheme illustrates the present invention:

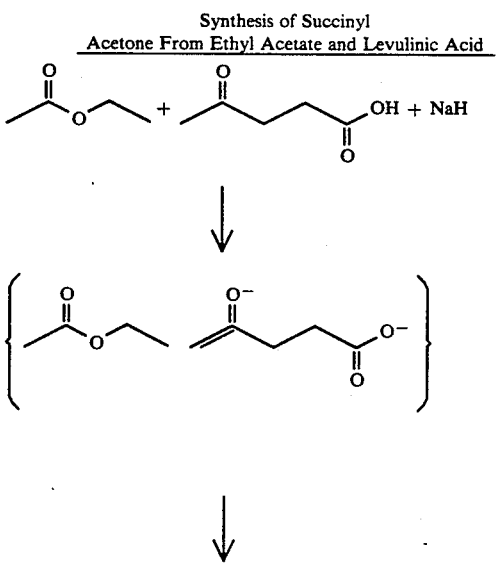

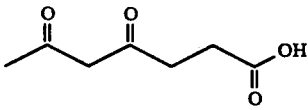

Once the SA is made it can be tested for activity using those assays known to those of skill in the art (for example see U.S. Ser. No. 324,360 which is hereby incorporated by reference in its entirety). Also it can be therapeutically used as shown in U.S. Ser. No. 324,360 either as a single compound or conjugated to other compounds to increase its therapeutic value.

The present process will now be illustrated by reference to the following examples which set forth particularly advantageous embodiments. However, it should be noted that these embodiments are illustrative and are not to be construed as restricting the invention in any way.

EXAMPLE 1

Synthesis of SA

A 500 ml three-neck round-bottom flask was flushed with argon and sodium hydride (oil free; 7.2 gm; 300 mmole) was introduced. Ethyl acetate (100 ml) was added and the suspension stirred while a solution of levulinic acid (11.6 gm; 100 mmole) in 30 ml ethyl acetate was added dropwise. Addition was made at such a rate that the evolution of hydrogen gas was moderate (monitored by a mineral oil-filled bubbler). The reaction warmed during the addition. When the addition was complete, the dropping funnel was removed and the mixture refluxed for one hour (or until evolution of hydrogen had ceased). To the cooled reaction mixture was carefully added 100 ml of water. Two layers formed. The aqueous layer was carefully acidified to pH 2.0 with conc. sulfuric acid. The mixture was transferred to a separatory funnel and shaken. The layers were separated and the aqueous layer saturated with sodium chloride. The aqueous phase was further extracted with ethyl acetate (3×100 ml) and the combined organic extracts dried over sodium sulfate, filtered and taken to dryness under reduced pressure. The residue was azeotroped with toluene (2×50 ml) and the crystalline residue taken up in 100 ml ether and filtered. Hexane (80 ml) was added to the filtrate and the opalescent mixture cooled. The crystals which formed were removed and redissolved in 100 ml ether and a teaspoonful of decolorizing charcoal added. The suspension was filtered and 60 ml of hexane added. Crystals formed and were collected by filtration and dried to yield 7 gms (44 mmole; 44%).

The present invention has been described with reference to specific embodiments. However, this application is intended to cover those changes and substitutions which may be made by those skilled in the art without departing from the spirit and the scope of amended claims.

What is claimed is:

1. A process for making Succinyl Acetone (SA) comprising reacting a levulinic acid group and an alkyl acetate, at the appropriate reaction conditions, in the presence of a base to make SA.

2. A process for making Succinyl Acetone in accordance with claim 1 wherein the acetylating reagent is an acetic acid ester.

3. A process for making Succinyl Acetone in accordance with claim 1 wherein the acetylating reagent is an alkyl acetate selected from the group consisting essentially of methyl acetate, ethyl acetate, and propyl acetate.

4. A process in accordance with claim 1 further comprising acidifying the SA containing reaction mixture.

5. A process in accordance with claim 1 wherein the base is selected from the group consisting essentially of lithium or sodium amide, sodium or potassium hydride, or sodium or potassium alkoxides.

6. A process in accordance with claim 4 wherein the acid is selected from the group consisting essentially of hydrochloric, sulfuric, phosphoric, and acetic acids.

7. A process in accordance with claim 6 wherein the base is selected from the group consisting essentially of lithium or sodium amide, sodium or potassium hydride, or sodium or potassium alkoxides.

8. A process in accordance with claim 6 wherein the acid is selected from the group consisting essentially of hydrochloric, sulfuric, phosphoric, and acetic acids.

9. A process in accordance with claim 5 wherein the alkoxides are selected from group consisting of methoxide, ethoxide, and t-butoxide.

10. A process in accordance with claim 7 wherein the base is selected from the group consisting essentially of lithium or sodium amide, sodium or potassium hydride, or sodium or potassium alkoxides.

11. A process for making Succinyl Acetone (SA) comprising reacting one part levulinic acid to at least three parts base in the presence of ethyl acetate, at the appropriate reaction conditions, to make SA, and acidifying the solution containing SA.

* * * * *